United States Patent [19]

Dutcher et al.

[11] 4,146,036

[45] Mar. 27, 1979

[54] BODY-IMPLANTABLE LEAD WITH PROTECTOR FOR TISSUE SECURING MEANS

[75] Inventors: Robert G. Dutcher, Columbia Heights; Albert S. Benjamin, White Bear Lake, both of Minn.

[73] Assignee: Medtronic, Inc., Minneapolis, Minn.

[21] Appl. No.: 839,954

[22] Filed: Oct. 6, 1977

[51] Int. Cl.$^2$ ............................................. A61N 1/04
[52] U.S. Cl. ................................. 128/418; 128/419 P
[58] Field of Search ......... 128/2.06 E, 2.1 E, DIG. 4, 128/404, 418, 419 P

[56] References Cited

U.S. PATENT DOCUMENTS

| | | | |
|---|---|---|---|
| 3,754,555 | 8/1973 | Schmitt | 128/418 |
| 3,976,082 | 8/1976 | Schmitt | 128/418 |
| 4,000,745 | 1/1977 | Goldberg | 128/418 |

FOREIGN PATENT DOCUMENTS 2533766  2/1977  Fed. Rep. of Germany ........... 128/418

Primary Examiner—William E. Kamm

Attorney, Agent, or Firm—Joseph F. Breimayer; Harry W. Barron

[57] ABSTRACT

A body-implantable, intravascular lead affixed with a pin or pins at its proximal end adapted to be connected to a pulse generator and with an electrode or electrodes at its distal end electrically connected via conductor means and adapted to be securely and permanently attached to a body organ. Electrode means in the form of an elongated member having a circumferential electrode formed on one end thereof and an opening passing therethrough from its proximal to distal end is affixed to the distal end of the conductor means. Tissue securing means extending beyond the opening in the distal end of the electrode means are provided for securing the electrode means into firm engagement with the tissue at the desired location. Movable means located in the opening in the electrode means are provided for protecting the tissue securing means from causing injury to a body vessel, heart valve, or other tissue as the lead is inserted and guided through a vessel to the desired location. Various types of stylet means may be used to move the movable means into the position for protecting the tissue securing means.

31 Claims, 7 Drawing Figures

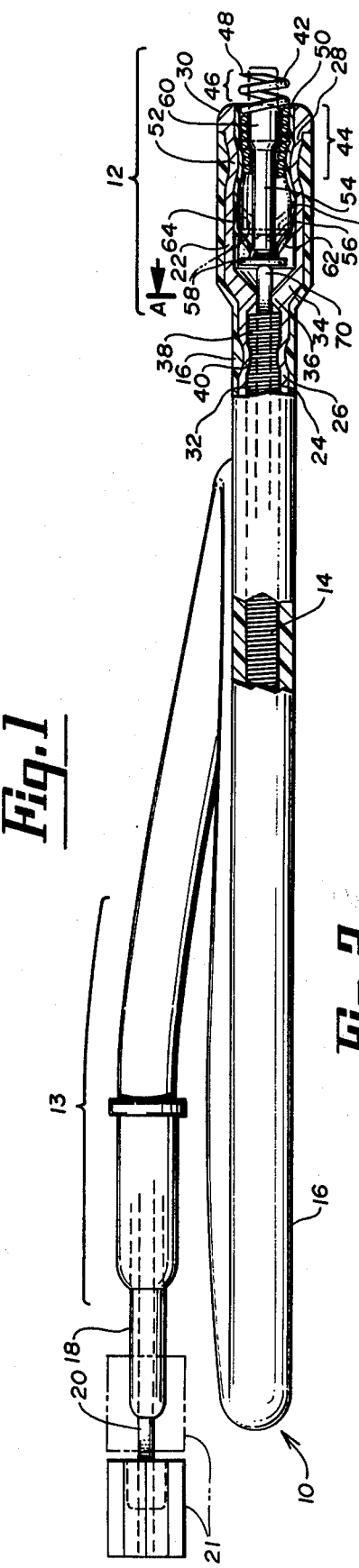
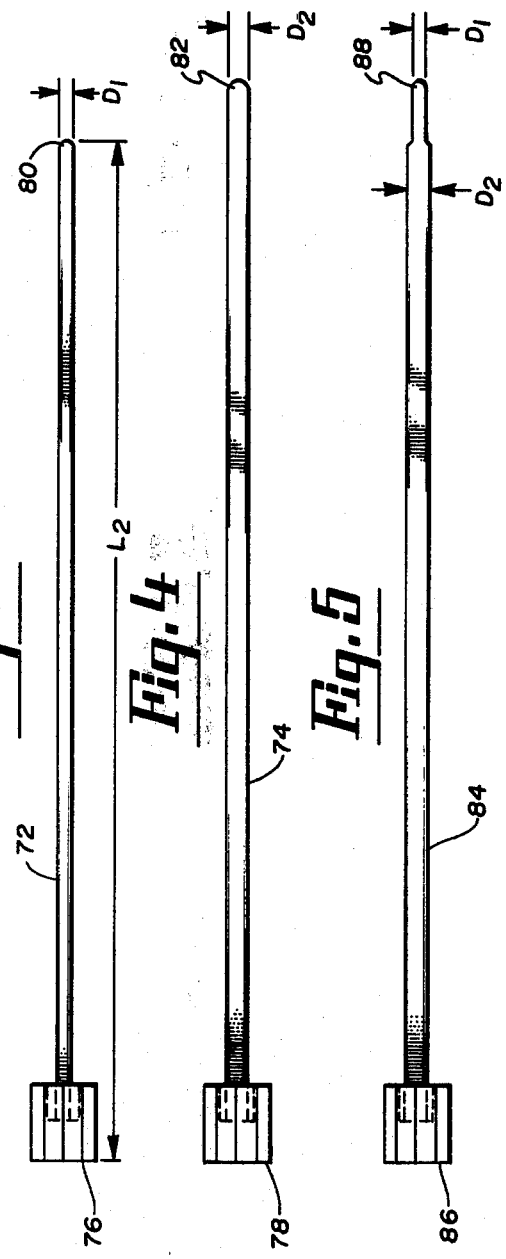
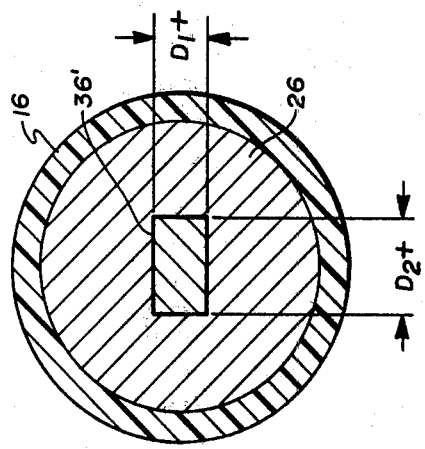

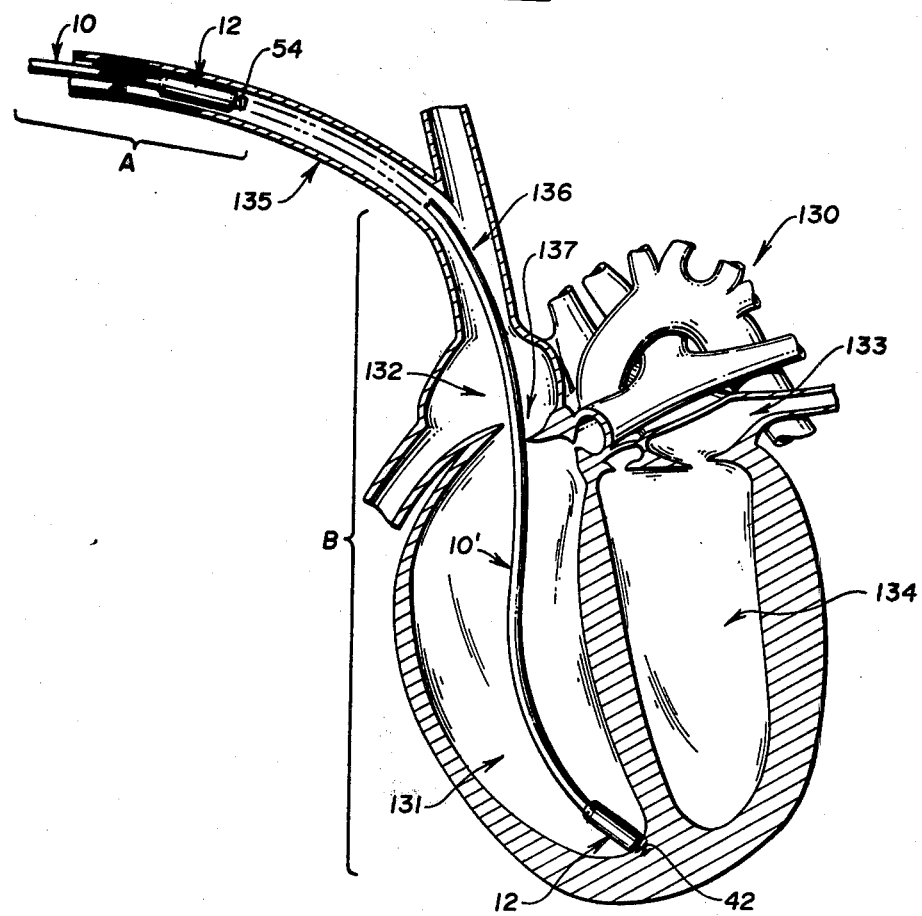

BODY-IMPLANTABLE LEAD WITH PROTECTOR FOR TISSUE SECURING MEANS

BACKGROUND OF THE INVENTION

This invention relates to a lead bearing an electrode for electrically connecting an organ inside a living animal body to an electrical device. Notwithstanding its various uses, this invention will be described for purposes of this description for use as an endocardial pacing and sensing lead for connecting an artificial cardiac pacemaker to cardiac tissue.

There are generally two types of body-implantable leads used with cardiac pacemakers — one which requires surgery to expose the myocardial tissue to which the electrode is in some manner or another affixed and another in which a lead with an electrode or electrodes located at its distal end is inserted in and guided through a body vessel such as a vein into the heart where the electrodes contact, and in some cases are secured to the heart through the endothelial tissue lining the inside of the heart. The former leads are generally referred to as myocardial type leads while the latter are generally referred to as endocardial type leads. Examples of prior myocardial leads may be found in U.S. Pat. No. 3,216,424, 3,416,534, 3,472,234, and 3,737,579. Examples of prior art endocardial leads may be found in U.S. Pat. No. 3,348,548, 3,754,555, 3,814,104, 3,844,292, and 3,974,834 and in publications such as "New Pacemaker Electrodes" by Max Schaldach appearing in Vol. 17 Transactions: American Society for Artificial Internal Organs, 1971, pp. 29–35; German Offenlegungsschrift No. 2,516,848 entitled "Transvenous Stimulation Electrode for Heart Pacemakers" published Oct. 28, 1976; and German Offenlegungsschrift No. 2,539,553 entitled "Electrode Assembly for Medical Purposes" published Mar. 10, 1977. These prior art teachings relate to various types of endocardial leads which are simple to manufacture and importantly are relatively easy to use by the implanting physician. The attributes of an endocardial lead which are most desirable are that the electrode be capable of being firmly secured into the wall of the cardiac tissue to prevent dislodgement while avoiding perforation of the electrode all the way through the cardiac tissue. In addition, it is important that the means used to secure the lead to the cardiac tissue be protected from causing damage to the vein, heart valve, or other tissue through which the lead is inserted into the heart. Other features of importance include electrodes having the desired shape and surface area requirements and means for securing the electrode to the heart without applying any permanent twisting or torque to the lead which will cause it to be stressed while in chronic use. Another problem with prior art leads has been that it is difficult to know exactly to what extent the means for securing the electrode to the cardiac tissue has been successfully achieved when the lead is in its final placement. Still another concern is, whether once in place, the electrode and/or securing means can be totally withdrawn out of the vein or at least disengaged from cardiac tissue and appropriately repositioned. The above cited prior art references have attempted with varying degrees of success to provide endocardial leads having some of the desirable features without any of the attendant problems or undesirable characteristics as described above.

The body-implantable lead of the present invention provides those features most desirable in an endocardial lead without those undesirable problems or characteristics. The present invention provides a body-implantable lead in which the electrode is of the desirable ring type having a desired shape and surface area. The electrode is a substantially elongated member having an opening passing therethrough in which is partially housed a helix. While the lead is being inserted and guided through the vein to the heart, the portion of the helix which extends out of the distal end of the electrode is prevented from causing any injury or damage to the vein, valve, or other tissues. Once in the desired location and position in the heart, the lead may be rotated so that the helix may very simply be screwed into the heart through the endocardial tissue. The helix once secured in place serves to hold the ring electrode in firm engagement with the cardiac tissue for providing the desired electrical stimulation as well as the detection to electrical signals from the heart. In the preferred embodiment the helix is electrically insulated from the electrode so that it serves only to secure the electrode in firm engagement with the tissue but in an alternate embodiment without the insulating member the helix may also be part of the electrode system if desired. Another feature of the present invention is that sealing means are provided in the opening in the electrode for preventing body fluids and tissue from reaching the proximal end of the electrode through the opening in the distal end.

SUMMARY OF THE INVENTION

The above features and advantages of the present invention, as well as others, are accomplished by providing a body-implantable lead having tissue securing means at the distal end thereof for securing an electrode in contact with tissue at a desired location and movable means for preventing the tissue securing means from causing injury as the lead is inserted in and guided through a body vessel to the desired location. The lead further comprises a proximal end adapted to be connected to a medical device, the tissue securing means and electrode means at the distal end thereof, and an electrical conductor extending therebetween encased in material means substantially inert to body fluids and tissue. The electrode means comprises a substantially elongated member having a chamber therein along its length. The tissue securing means are located partially within and extending beyond at the distal end of the electrode means for securing the electrode means in firm engagement with the endocardial tissue at the desired location. Sealing means located in the chamber are provided for preventing body fluids and tissue from reaching the proximal end of the electrode means through the lumen extending to the distal end of the electrode means. The movable means positioned within the chamber are provided for protecting the tissue securing means from causing injury to the body vessel, valve or other tissues as the lead is inserted and guided through a body vessel to the desired location.

Preferably, the tissue securing means is a helix having several spaced turns. The movable means is an elongated cylindrical rod located in the chamber in the electrode means. The distal end of the rod is positioned within the coils at the proximal end of the helix. A stylet pressure fit at its proximal end to the proximal end of the lead passes through the lumen defined by the conductor coil comprising the conductive lead means. The lumen communicates with the opening in the proximal end of the electrode means such that the distal end of the stylet when fully inserted passes into the opening in the proximal end of the electrode means and engages the proximal end of the rod moving the distal end of the rod out of the opening at the distal end of the electrode means and within the coils of the helix extending beyond the distal end of the electrode means. In this manner the point and turns of the helix extending beyond the distal end of the electrode means are protected from causing injury or damage to the vein, valve, or other tissues as the lead is inserted and guided to the desired location. Once the lead is at the desired location the first stylet is totally withdrawn from the lead freeing the rod for automatic retraction back into the chamber in the distal end of the electrode means. A second stylet, which cannot contact the rod either because it is not long enough or of sufficiently large cross-sectional diameter that it does not pass through the opening in the proximal end of the electrode means, is inserted in the lead. The lead is then rotated a desired amount causing the helix to be screwed into the endocardial and myocardial tissues to secure and permanently maintain the ring electrode in the desired contact with the tissue. Other features, advantages and objects of the present invention will hereinafter become more fully apparent from the following description of the drawings, which illustrate the invention.

BRIEF DESCRIPTION OF THE DRAWINGS

FIG. 1 shows a view of a preferred embodiment of the body-implantable, intravascular lead of the present invention including in part an inside elevation partly in longitudinal section of the electrode end portion of the lead;

FIGS. 2 through 5 show stylets useable in conjunction with the lead of the present invention;

FIG. 6 shows a cross section viewed of a keyway defining the opening into which the correspondingly shaped end of the stylet of FIG. 6 may be placed; and FIG. 7 shows the lead of FIG. 1 being lodged in and permanently secured to the tissue forming the apex of the right ventricle of the heart.

DESCRIPTION OF THE PREFERRED EMBODIMENT

Referring now to the preferred embodiment of the invention depicted in FIG. 1, there is shown an intravascular endocardial lead comprising an elongated lead portion 10, a distal electrode end portion 12 and a proximal terminal end portion 13. The lead, in unipolar configuration, comprises a closely wound, coiled conductor 14 in the form of a spring spirally wound about and along the axis of the conductor. The spring coil 14 extends through the length of the lead 10 in a lumen of a jacket or sleeve 16 of electrically insulating material.

The spiral conductor 14 is formed of electrically conductive material offering low electrical resistance and also resistant to corrosion by body fluids. A platinum-iridium alloy is an example of a suitable material. Sleeve 16 is formed of an electrically insulating material, and preferably a silicone rubber such as clean room grade Silastic available from Dow Corning Corporation or a polyether urethane such as Pellethane ® CPR ® 2363-80AE available from the Upjohn Company. These materials are additionally suitable because they are inert and well tolerated by body tissue.

At the proximal end 13 of the lead 10, the conductor 14 is received in and crimped to tubular terminal pin 18. Terminal pin 18 projects beyond sleeve 16 and is adapted for insertion in receptacles provided on the pulse generator, which can comprise any suitable implantable pulse generator such as that shown for example in U.S. Pat. No. 3,057,356.

The pin 18 and the spiral conductor 14 are hollow defining a lumen and thereby adapted to receive a stiffening stylet 20 that extends through the length of the lead 10. The stylet 20 stiffens the lead 10, and its proximal end, adjacent the proximal end 13 of the lead, is formed to provide means, such as the knob 21, which is knurled on its outer surface for rotating the stylet about its axis to thereby direct the distal end 12 of the lead as it is inserted through the vein. The stylet imparts rigidity to the proximal portion of the leads and can be manipulated to introduce an appropriate curvature to the distal, electrode end portion facilitating the insertion of the lead into and through a vein and through an intracardiac valve, for example one of the jugular veins and the tricuspid valve, to advance the distal end 12 of the led into the right ventricle of the heart. In the present invention two different stylets are used, each having a slightly different purpose as will hereinafter be explained.

At the distal end of the lead 10 an electrode body in the form of an elongated member 22 is provided. Electrode body 22 has an opening 24 which passes completely therethrough along its longitudinal axis from its proximal end 26 to its distal end 28. Integrally formed as part of electrode body 22 and located at its distal end 28 is a raised portion 30 which serves as the ring electrode of lead 10. The outer surface of ring electrode 30 is somewhat rounded and smooth having the desired shape and surface area for the required stimulation and detection of electrical signals from the heart. Electrode body 22 in the preferred embodiment is a substantially cylindrical member having a circular cross section but may take a number of other configurations. Electrode body 22, preferably is made of a corrosion resistant, electrically conductive material, e.g., platinum or a platinum alloy, a metal oxide or a carbon compound. In the specific embodiment shown, electrode 22 is made of a platinum-iridium alloy. The entire outer surface of electrode body 22 except the raised portion forming ring electrode 30 is insulated as shown by the continuous covering provided by sleeve 16 which conforms to the shape of the outer surface of electrode body 22. In this way the entire lead is electrically insulated when it is connected to the pulse generator from the body except at the ring electrode 30.

Opening 24 passing through electrode body 22 is sectioned into two chambers 32 and 34. Chamber 32 located at the proximal end 26 of electrode body 22 is somewhat smaller in cross section than chamber 34 which is located toward the distal end 28. A restriction 36 is provided on the inner surface of opening 24 and located between the chambers 32 and 34.

Distal end 38 of conductor coil 14 is located in chamber 32 whereby the lumen defined by coil 14 communicates with the distal end of chamber 32 and with chamber 34 located on the distal side of restriction 36. The distal end 38 of coil 14 is physically maintained, and mechanically and electrically connected to electrode body 22 via a crimped portion 40 in the proximal end 26 of electrode body 22. This mechanical connection between coil 14 and electrode body 22 could be accomplished in ways other than crimping.

Coil 14 is of a well known construction similar to the conductor coils disclosed in U.S. Pat. Nos. 3,348,548 and 3,974,834. A lead such as 10 using a conductor coil such as coil 14 has been shown to be capable of withstanding constant, rapidly repeated flexing over a period of time which can be measured in years. The conductor coil is wound relatively tightly, although there can be a slight space between adjacent turns. This closely coiled construction provides a maximum number of conductor turns per unit length, thereby providing optimum strain distribution. The spirally coiled spring construction of conductor 14 also permits a substantial degree of elongation, within the elastic limits of the material, as well as distribution along the conductor of flexing stresses which otherwise might be concentrated at a particular point. Both the conductor 14 and the insulating sleeve 16 are elastic, and this, together with the coiled construction of the conductor, assures maximum distribution of flexing strains. Conductor 14 may also comprise a multi-filar redundant coil of thinner, highly elastic wire.

A tissue securing member in the form of a relatively rigid circular corkscrew or helix 42 is provided having a proximal end 44 of several closely wound turns located in the chamber 34 at the distal end 28 of electrode body 22. Helix 42 has a distal end 46 formed by about two spaced turns which extend out of chamber 34 beyond the end of ring electrode 30 approximately 0.08 inches. These turns end in a sharpened tip 48 at a point on the inside circumference of the wire making up helix 42. An insulating hollow sleeve 50 is provided tightly fitting in at the distal end 28 inide chamber 34. Sleeve 50 may be made of Delrin ® or other suitable body compatible, insulating material. A crimp is provided in electrode body 22 near its distal end 28 at crimped portion 52. Crimped portion 52 serves to hold proximal end 44 of helix 42 in fixed position from lateral or rotational movement by squeezing or crimping the adjacent portion of sleeve 50 and several closely wound turns at the proximal end 28 of helix 42. Again, this fixing of helix 42 in position could be accomplished in other ways than by crimping. Sleeve 50 serves to help fix helix 42 in place as well as insulate helix 42 from electrode body 22 so that helix 42 serves only as a means of securing and maintaining ring electrode 30 in firm engagement with endocardial tissue as will later be described. In this arrangement helix 42 forms no part of the electrode structure. Of course, if it were desired in certain applications that helix 42 form a part of the electrode structure, this could be accomplished by eliminating insulating sleeve 50. Helix 42 in its uncrimped section 46 has a nominal outside diameter of approximately 0.06 inches with the nominal outside diameter of sleeve 16 and ring electrode 30 being about 0.13 inches. Helix 42 is a platinum-iridium coil made of approximately 0.012 inch outer diameter wire.

Also provided in chamber 34 is an elongated plunger or rod 54 which is generally circular in cross section. Rod 54 may be made of Delrin ® plastic or any other suitable body compatible material such as a hardened epoxy, nylon or urethane. Rod 54 has a proximal end 56 at which is located a flattened head 58 and a distal end 60 which is somewhat greater in cross-sectional diameter than proximal end 56 of rod 54. Distal end 60 of rod 54 provides a relatively close fit within the portion of helix 42 distally of the crimped turns at proximal end 44 as well as within the spaced turns of distal end 46 of helix 42. In its unextended position distal end 60 remains totally within chamber 34 and does not extend beyond the distal end of electrode body 22.

A boot 62 is provided in chamber 34 near head 58 of rod 54. This boot 62 has a leg portion 64 which extends outwardly from rod 54 and fits tightly against the inner surface of chamber 34. Boot 62 may snap tightly and fit onto rod 62 or may be secured in a groove provided on the outer surface of rod 54 near head 58. Leg 64 has an end portion 66 extending from the end of leg 64 which fits against and under the proximal end of sleeve 50. Boot 62 may be made of a silicone rubber or other body compatible, flexible material. Boot 62 serves to seal off body fluids and tissue coming into chamber 34 at the distal end 28 of electrode body 22 from reaching chamber 32 or the distal end 38 of coil 14. Boot 62 is sufficiently flexible so as to allow movement of rod 54 whereby distal end 60 of rod 54 moves distally outward from chamber 34 beyond the end of ring electrode 30 through the spaced turns all the way to the very distal end of helix 42 as shown in dotted lines, the purposes of which will be later explained in conjunction with the operation of the present invention.

It will be understood from the following description that the boot 62 as shown in FIG. 1 is compressed upon itself as distal end 70 of stylet 20 bears against head 58 of rod 54, to move rod 54 to its advanced position. In a further embodiment (not illustrated), the cylindrical boot 62 may be fixed at one of its ends near the restriction 36 and at its other end to the distal side of the head 58 nearest helix 42. In this second embodiment, the body of the boot would be stretched as the end 70 advances the rod 54 into the advanced position and would also provide the requisite sealing of the lead body within conductor 14 from body fluids and tissue.

FIGS. 2 through 5 show stylets that may be used in conjunction with the lead 10 of the present invention. Stylet 20 shown inserted in lead 10 in FIG. 1 has a length $L_1$ and a cross sectional diameter $D_1$. When fully inserted in lead 10 through terminal pin 18 knurled knob 21 of stylet 20 is pressure fit on the end of pin 18. Length $L_1$ of stylet 20 passes through the lumen defined by coil 14 and as seen in FIG. 1, stylet 20 has a distal end 70 which presses against head 58 of rod 54. When fully inserted the distal end 70 of stylet 20 moves the distal end 60 of rod 54 out of the distal end 28 of electrode body 22 and beyond ring electrode 30 into the dotted position shown in FIG. 1. In this extended position, distal end 60 of rod 54 serves to protect the tip 48 and spaced turns at distal end 46 of helix 42 from causing any damage to the vein, valve or other tissue through which lead 10 is inserted and guided. Thus stylet 20 serves to move rod 54 into its extended protective position as shown dotted in FIG. 1.

A second stylet may then be required to be used for screwing distal end 46 of helix 42 into endocardial and myocardial tissue. Either stylet 72, 74, or 84 may be used for this purpose. These stylets each have knurled knobs 76, 78 and 86 respectively fixed on the proximal ends thereof. The knobs are all the same as knob 21 on stylet 20. Stylets 72, 74 and 84 are made so as to be readily visibly and tactilly distinguishable from stylet 20. Stylet 72 has the same cross section diameter $D_1$ as stylet 20 but has a shorter length $L_2$ than the length $L_1$ of stylet 20. Length $L_2$ is sufficiently shorter than length $L_1$ of stylet 20 that when stylet 72 is fully inserted into lead 10, its distal end 80 does not reach or contact rod 54 so that rod 54 remains in its retracted or unextended position wholly within electrode body 22. Stylet 72 thus allows the tip 48 of helix 42 and the spaced turns at distal end 46 of helix 42 to pierce endocardial tissue and allows a sufficient portion of the spaced turns to be screwed into the tissue as stylet knob 76 and proximal end 13 of lead 10 are rotated. Helix 42 thereby advances through endocardial tissue into myocardial tissue to be retained therein and inhibited from dislodgement therefrom by the spaced turns at the distal end 46 of helix 42. In such position ring electrode 30 is secured in position to firmly maintain contact with the cardiac tissue to permit appropriate electrical stimulation and detection of electrical signals to take place through ring electrode 30. Alternatively to stylet 72, stylet 74 is provided, which although having the same length $L_1$ as stylet 20 has a cross-sectional diameter $D_2$ somewhat greater than diameter $D_1$ of stylet 20. Because of this greater diameter $D_2$ when stylet 74 is inserted in lead 10, the distal end 82 is unable to pass through restriction 36 and therefore cannot reach rod 54, leaving rod 54 in its unextended position. Stylet 74 is then used to secure helix 42 into endocardial tissue in the same manner as described above with respect to stylet 72.

The stylet 84 of FIG. 5 has a main body diameter of $D_2$ and a distal end portion 88 that is flattened to have a cross section that may be the same dimension as $D_1$. FIG. 6 depicts a cross section of the distal end 12 of lead 10 at the restriction 36. The restriction 36' depicted in FIG. 6 is rectangular in shape having dimensions $D_1+$ and $D_2+$ closely slightly larger than those dimensions $D_1$ and $D_2$ of the portion 88 of stylet 84. In use, the distal portion 88 extends through restriction 36 to extend rod 54 in the manner herein described and, upon partial retraction allows the rod to retract when the helix is to be screwed in. The key relationship of restriction 36' and portion 88 allows torque to be transmitted directly from knob 86 to restriction 36' to facilitate screwing the helix into the heart.

A mark at the proximal end of the stylet 84 may be provided to show the amount by which the stylet should be withdrawn to allow rod 54 to retract. In addition rod 54 may be made with a radio-opaque material so that its position may be determined during insertion under fluoroscopy. Of course, restriction 36' and portion 88 could have other matching or keyed configurations.

Turning now to FIG. 7, there is shown an illustration of the partially introduced lead 10 of the present invention in a vein (position A) and the completed introduction and permanent securement of the helix 42 in the tissue forming the apex of the right ventricle of a heart (position B).

In FIG. 7, the heart 130 in cross section comprises the four chambers, namely, the right ventricle 131, the right atrium 132, the left atrium 133 and the left ventricle 134. In the placement of an endocardial lead, it is preferable to use a venous approach on the low pressure side of the heart, that is, through a vein, e.g., the right or left external jugular veins or the right or left cephalic veins 135, the superior vena cava 136, the right atrium 132, the tricuspid valve 137 and the right ventricle 131. During introduction of the lead 10, it must travel a convoluted course through the veins and must pass through the valve 137 without causing any damage to the tissue. It is also desirable that the lead 10 have a small cross section so that it will easily pass through the veins without causing excessive stretching of the veins.

In position A of FIG. 7, the distal end 12 of lead 10 is shown in part. To get to this position stylet 20 is fully inserted in proximal end 13 of lead 10 with knob 21 pressure fit on the end of terminal pin 18. In this position distal end 70 of stylet 20, for example, presses against head 58 of rod 54 moving the rod into its extended position. In extended position, distal end 60 of rod 54 is located inside the spaced turns at the distal end 46 of helix 42 and extends past the tip 48. In this extended position the distal end 60 of rod 54 serves to protect the spaced turns at distal end 46 and point 48 of helix 42 from causing any damage to the vein, the superior vena cava 136, the right atrium 132, valve 137 or right ventricle 131 as lead 10 is inserted into vein 135 and guided into the apex at the bottom of the right ventricle 131 or in other suitable sites in the right ventricle or right atrium.

Once lead 10 is appropriately situated, for example in the apex of the right ventricle 131 as seen in position B, stylet 20 is withdrawn from lead 10, causing rod 54 to automatically be retracted back inside chamber 34 into its unextended position. Then either of stylets 72 or 74 is inserted through pin 18 into lead 10. As described earlier, the distal ends 80 or 82 of these respective stylets do not contact rod 54 so that the rod remains in its retracted or unextended position totally within chamber 34 of electrode body 22. Therefore tip 48 and the spaced turns at the distal end 46 of helix 42 are ready to be screwed into the endocardial tissue in the apex of the right ventricle or other suitable location. Knob 76 or 78 and proximal end 13 of lead 10 are rotated causing tip 48 to pierce the endocardial tissue and the spaced turns of helix 42 are fully screwed into myocardial tissue by the continued rotation. Alternatively, the lead 10 may be turned about the stylet 72 or 74 to screw in the helix 42. Once fully screwed into the myocardial tissue the ring electrode 30 is secured into firm engagement with the tissue for providing the electrical stimulation and detection of electrical signals. In the event that for any reason rod 54 was not automatically retracted back inside chamber 34 when stylet 20 was completely withdrawn, the screwing of helix 42 into the tissue will cause the rod to be retracted back into chamber 34 to its unextended position. Once lead 10 is in secured position, the stylet 72 or 74, whichever was used is fully withdrawn from the lead.

In removing lead 10 from its secured position as seen in position B, first either stylet 72 or 74 is inserted and by manipulation of knob 76 or 78 respectively and the proximal end 13 of lead 10, the helix 42 is unscrewed from the tissue. Of course, rod 54 remains in its retracted or unextended position. Once helix 42 is unscrewed, stylet 20 is fully reinserted into lead 10 so that distal end 70 moves rod 54 into its extended position. Tip 48 and the spaced turns at the distal end 46 of helix 42 extending out of ring electrode 30 are protected so that as lead 10 is withdrawn out of the ventricle 131, back through valve 137, atrium 132, superior vena cava 136 and vein 135, no damage or injury to any of this tissue is caused.

In vivo testing of lead 10 reveals that the helix can be easily and repeatedly introduced through the vein, through the valve and screwed into the endocardium, unscrewed and withdrawn from the body through the same path without causing any significant damage to the tissue that the lead contacts. The ease of using the lead of the present invention and the positive securement afforded by a corkscrew or helix together with the extendable protective rod make it very desirable compared to many prior endocardial lead designs.

Although a unipolar lead design has been illustrated in the description of the preferred embodiment, it will be understood that bipolar leads (that is a lead carrying two electrodes and conductors) may as readily employ the novel protective rod-ring electrode design of the present invention. It should be understood that although the use of the lead 10 has been described for use in a cardiac pacing system, lead 10 could as well be applied to other types of body stimulating systems.

It should be further understood, of course, that the foregoing disclosure relates only to the best mode known to the inventor of many possible modes of practicing the invention and that numerous modifications may be made therein without departing from the spirit and scope of the invention as set forth in the appended claims.

What is claimed is:

1. A body-implantable lead adapted to be connected at its proximal end to a medical device and secured at its distal end to tissue of a living body for electrical stimulation thereof and for detecting electrical signals comprising:

an electrical conductor extending between the proximal and distal ends of said lead;

an electrode body at the distal end of said lead having electrode means exposed to body tissue and electrically connected to the distial end of said conductor and adapted to supply electrical impulses to and receive electrical signals from tissue at a desired location inside the living body, said electrode body having a chamber therein with an opening at the distal end of said lead body;

material means substantially inert to body fluids and tissue encasing said conductor;

tissue securing means extending from the distal end of said electrode body for securing said electrode means in contact with tissue at the desired location; and movable means fitting in a retracted position within said chamber and movable to an extended position extending from said opening and adjacent said tissue securing means for preventing said tissue securing means from causing injury as said lead is inserted and guided through a body vessel to the desired location.

2. The body-implantable lead of claim 1 wherein said electrode means comprises a cylindrical member having a proximal and distal end defining said chamber therein, and wherein said material means encases all but at least a portion of said cylindrical member.

3. The body-implantable lead of claim 2 further comprising:

a lumen extending between the proximal end of said lead and said chamber.

4. The body-implantable lead of claim 3 wherein said movable means comprises a member located in said chamber, adapted to be engaged via said lumen for extending a portion of said member beyond said opening to said extended position.

5. An assembly of the body-implantable lead of claim 4 with a stylet comprising:

first stylet means insertable through said lumen and to said chamber so as to be engageable with the proximal end of said member to move said portion of said member into said extended position adjacent said tissue securing means to prevent damage to a body vessel.

6. The assembly of claim 5 further comprising:

means for automatically retracting said member back into said chamber when said first stylet means is withdrawn from engagement with said member.

7. The assembly of claim 5 wherein said first stylet means further comprises:

means located at the proximal end of said stylet means pressure fittable to the proximal end of said lead when said stylet means is fully inserted into said lumen so that the distal end of said stylet means maintains said member in its extended position.

8. The assembly of claim 5 further comprising:

second stylet means insertable into said lumen but not engageable with said member to facilitate attachment of said tissue securing means to tissue once said electrode means is at the desired location and said first stylet means has been entirely withdrawn from said lumen.

9. The assembly of claim 8 wherein said second stylet means is sufficiently shorter than said first stylet means so that said second stylet means does not contact said member when said second stylet means is fully inserted into said lumen of said lead.

10. The assembly of claim 8 wherein said cylindrical member has a narrowed proximal end portion intermediate said lumen and said chamber;

said first stylet means is smaller in cross section than said narrowed portion and can pass therethrough for moving said member into its extended position; and said second stylet means is greater in cross section than said narrowed portion and cannot pass therethrough.

11. The body-implantable lead of claim 1 further comprising:

sealing means located in said chamber for preventing body fluids and tissue from reaching said conductor.

12. The body-implantable lead of claim 11 wherein said sealing means comprises a boot tightly fit around the proximal end of said movable means and pressure fit in said chamber, said boot preventing the entry of body fluids and tissue into said lead, beyond said chamber, while at the same time allowing movement of said movable means to said extended position.

13. The body-implantable lead of claim 12 wherein said boot further comprises resilient means adapted to resist the movement of said movable means to said extended position and to automatically return said movable means to said retracted position.

14. A body-implantable lead adapted to be connected at its proximal end to a medical device and secured at its distal end to tissue of a living body for electrical stimulation thereof and for detecting electrical signals comprising:

an electrical conductor extending between the proximal and distal ends of said lead;

an electrode body at the distal end of said lead having electrode means exposed to body tissue and electrically connected to the distal end of said conductor and adapted to supply electrical impulses to and receive electrical signals from tissue at a desired location inside the living body, said electrode head means having a chamber therein with an opening at the distal end of said lead body;

material means substantially inert to body fluids and tissue encasing said conductor;

helical tissue securing means extending axially from the distal end of said electrode head means adapted to be screwed into body tissue for securing said electrode means in contact with tissue at the desired location; and movable means fitting in a retracted position within said chamber and movable to an extended position extending from said opening and within said helical tissue securing means for preventing said helical tissue securing means from causing injury as said lead is inserted and guided through a body vessel to the desired location.

15. The body-implantable lead of claim 14 wherein said helical tissue securing means comprises a point at its distal end for piercing tissue and at least one spaced tissue securing turn.

16. The body-implantable lead of claim 15 wherein said electrode means comprises a cylindrical member having a proximal and distal end defining said chamber therein, said material means encasing all but at least a portion of said cylindrical member.

17. The body-implantable lead of claim 16 wherein said helical tissue securing means further comprises several closely spaced turns proximal to said widely spaced turn and secured within said chamber.

18. The body-implantable lead of claim 16 wherein said portion comprises a ring electrode at the distal end of said lead.

19. The body-implantable lead of claim 14 wherein said conductor comprises a conductor coil defining a lumen which communicates with said opening in said electrode lead means.

20. The body-implantable lead of claim 19 wherein said moveable means comprises a rod located in said opening, adapted to be engaged via the lumen defined by said coil for extending a portion of said rod beyond said opening to said extended position at least to the distal end of said helical tissue securing means.

21. The body-implantable lead of claim 20 wherein said portion of said rod is of greater cross-section than the rest of said rod and is only slightly smaller than the inside diameter of said helical tissue securing means.

22. An assembly of the body-implantable lead of claim 20 and a stylet comprising:
first stylet means insertable through the lumen of said coil and to said chamber so as to be engageable with the proximal end of said rod to move said portion of said rod into said extended position.

23. The assembly of claim 22 further comprising:
means for automatically retracting said rod back into said opening when said first stylet means is withdrawn from engagement with said rod.

24. The assembly of claim 22 wherein said first stylet means further comprises:
means located at the proximal end of said stylet means adapted to be coupled to the proximal end of said lead when said stylet means is fully inserted into said lumen so that the distal end of said stylet means maintains said rod in its extended position.

25. The assembly of claim 22 further comprising:
second stylet means insertable into said lumen but not engageable with said rod to facilitate screwing said helical tissue securing means into tissue once said electrode means is at the desired location and said first stylet means has been entirely withdrawn from said lumen.

26. The assembly of claim 25 wherein said second stylet means is sufficiently shorter than said first stylet means so that said second stylet means does not contact said rod when said second stylet means is fully inserted into said lead.

27. The assembly of claim 25 wherein said cylindrical member has a narrowed proximal end portion intermediate said lumen and said chamber;
said first stylet means is smaller in cross-section than said narrowed portion and can pass therethrough for moving said rod into its extended position; and
said second stylet means is greater in cross-section than said narrowed portion and cannot pass therethrough.

28. The body-implantable lead of claim 14 wherein said opening has narrow key engageable means and further comprising:
stylet means having a keyed distal tip for insertion through said lumen of said coil and into said key engageable means for enabling rotational torque applied at the proximal end of the stylet means to be directly coupled to the distal end of said lead to screw said helical tissue securing means into body tissue.

29. The body-implantable lead of claim 14 further comprising:
sealing means located in said chamber for preventing body fluids and tissue from reaching said conductor.

30. The body-implantable lead of claim 29 wherein said sealing means comprises:
a boot tightly fit around the proximal end of said movable means and pressure fit in said chamber, said boot preventing the entry of body fluids and tissue into said lead, beyond said chamber, while at the same time allowing movement of said movable means to said extended position.

31. The body-implantable lead of claim 30 wherein said boot further comprises resilient means adapted to resist the movement of said movable means to said extended position and to automatically return said movable means to said retracted position.

* * * * *